(12) United States Patent
Ferrieux

(10) Patent No.: US 10,918,756 B2
(45) Date of Patent: Feb. 16, 2021

(54) SOLID NON-AQUEOUS GEL AIR ODORIZER

(71) Applicant: Dow Global Technologies LLC, Midland, MI (US)

(72) Inventor: Severine Ferrieux, Grasse (FR)

(73) Assignee: Dow Global technologies LLC, Midland, MI (US)

( * ) Notice: Subject to any disclaimer, the term of this patent is extended or adjusted under 35 U.S.C. 154(b) by 29 days.

(21) Appl. No.: 16/340,236

(22) PCT Filed: Oct. 13, 2017

(86) PCT No.: PCT/US2017/056445
§ 371 (c)(1),
(2) Date: Apr. 8, 2019

(87) PCT Pub. No.: WO2018/085021
PCT Pub. Date: May 11, 2018

(65) Prior Publication Data
US 2020/0038538 A1    Feb. 6, 2020

(30) Foreign Application Priority Data

Nov. 2, 2016  (EP) .................... 16290211

(51) Int. Cl.
*A61L 9/04*      (2006.01)
*A01M 29/12*   (2011.01)

(52) U.S. Cl.
CPC ............. *A61L 9/042* (2013.01); *A01M 29/12* (2013.01); *A61L 9/044* (2013.01); *A61L 9/048* (2013.01)

(58) Field of Classification Search
CPC .......... A61L 9/042; A61L 9/048; A61L 9/044; A61L 9/012; A01M 29/12
See application file for complete search history.

(56) References Cited

U.S. PATENT DOCUMENTS

| 2,865,806 | A | | 12/1958 | Bulloff |
| 3,485,915 | A | * | 12/1969 | Gerstein ............... A61Q 5/06 514/772.6 |
| 4,067,824 | A | | 1/1978 | Teng et al. |
| 4,128,507 | A | | 12/1978 | Mitzner |
| 4,587,129 | A | | 5/1986 | Kliment |
| 4,617,147 | A | | 10/1986 | Shibanai |
| 4,888,364 | A | | 12/1989 | Graiver et al. |
| 5,093,182 | A | | 3/1992 | Ross |
| 5,562,850 | A | | 10/1996 | Woo et al. |
| 7,235,187 | B2 | | 6/2007 | Li et al. |
| 7,485,610 | B2 | | 2/2009 | Heinz et al. |
| 2004/0180067 | A1 | | 9/2004 | Popplewell et al. |
| 2005/0004329 | A1 | | 1/2005 | Thorman |
| 2005/0274817 | A1 | | 12/2005 | Maat |
| 2006/0067859 | A1 | | 3/2006 | Laudamiel-Pellet et al. |
| 2006/0249592 | A1 | | 11/2006 | Burrowes et al. |
| 2010/0310492 | A1 | | 12/2010 | Stalet et al. |
| 2011/0318296 | A1 | | 12/2011 | Braun et al. |
| 2013/0012634 | A1 | | 1/2013 | Gauthy et al. |
| 2013/0202788 | A1 | | 8/2013 | Mikkelsen et al. |

FOREIGN PATENT DOCUMENTS

GB    2363717 A    1/2002

* cited by examiner

*Primary Examiner* — Mina Haghighatian
(74) *Attorney, Agent, or Firm* — Thomas S. Deibert

(57) ABSTRACT

A solid non-aqueous gel air odorizer is provided, including: a poly(propylene oxide); an ethyl cellulose polymer; a $C_{1-5}$ alkyl monoester of a $C_{8-22}$ fatty acid; and a fragrance; wherein the solid non-aqueous gel air odorizer contains <1.5 wt % water.

8 Claims, 1 Drawing Sheet

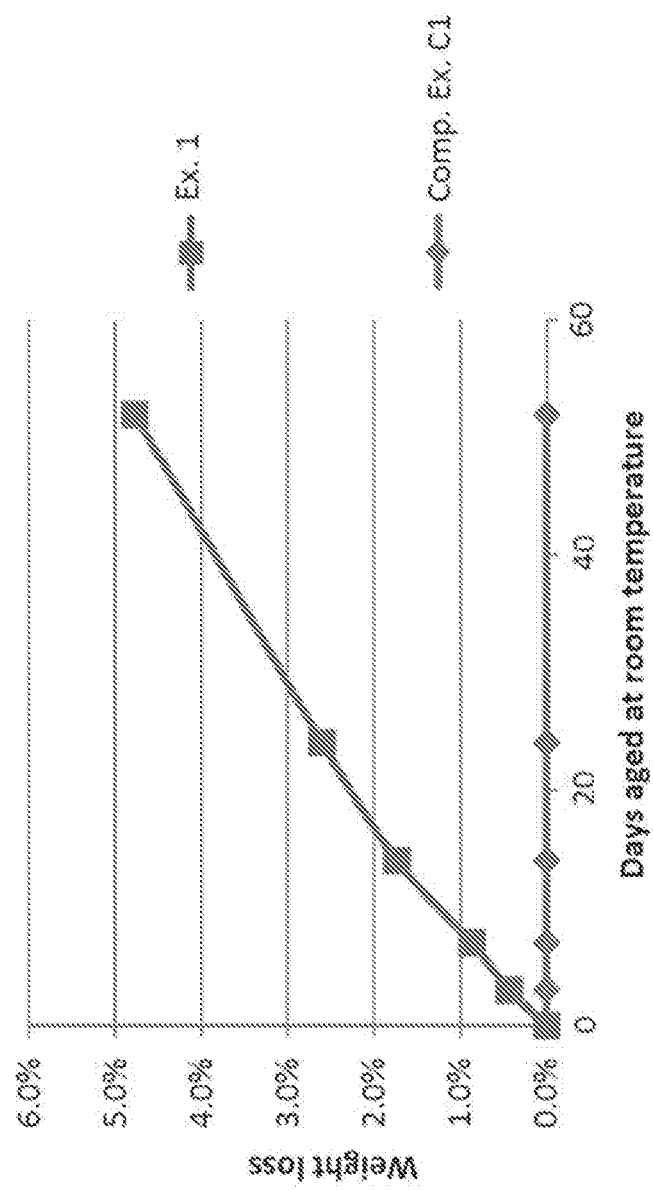

SOLID NON-AQUEOUS GEL AIR ODORIZER

The present invention relates to a solid non-aqueous gel air odorizer. In particular, the present invention relates to a solid non-aqueous gel air odorizer is provided, including: a poly(propylene oxide); an ethyl cellulose polymer; a $C_{1-5}$ alkyl monoester of a $C_{8-22}$ fatty acid; and a fragrance; wherein the solid non-aqueous gel air odorizer contains <1.5 wt % water.

Room malodor control devices capable of releasing a deodorant or fragrance into the space surrounding the device exist in the marketplace. Some such devices include fragrance holders that are inserted in a housing or shell through which ambient air is allowed access through openings such that the fragrance may be introduced into the air. Other such devices comprise a matrix impregnated with the deodorant or fragrance.

Conventional room malodor control devices release fragrance into the surroundings for a period of time before needing to be replaced, but seldom offer adequate visual indication to the user that replacement is required before the device is depleted.

Many conventional room malodor control devices suffer from having a short useful lifetime and from exhibiting an inconsistent release rate of the fragrance over the device lifetime.

A solid air freshener is disclosed by Braun et al. in U.S. Patent Application Publication No. 20110318296. Braun et al. disclose a solid air freshener comprising the following components: i) a total amount of polyethylene glycols in the range of from 30 to 80 wt %, wherein the weight average molecular weight, Mw, of the total amount of polyethylene glycols present in the solid air freshener is in the range of from 1000 to 20000 g/mol, the total amount of polyethylene glycols consisting of one, two, or more polyethylene glycol materials, ii) a total amount of surfactants in the range of from 5 to 40 wt %, iii) a total amount of perfume in the range of from 5 to 50 wt %, wherein the perfume consists of (a) fragrance material, and optionally (b) a solvent for the fragrance material, iv) an amount of water in the range of from 0 to 10 wt %, wherein any water present in the solid air freshener is exclusively considered as component (iv), and wherein the total amount of components (i), (ii), (iii), and (iv) is at least 95 wt %, based on the total weight of the solid air freshener.

Perfumed gels of hydroxypropyl cellulose are disclosed by Mitzner in U.S. Pat. No. 4,128,507. Mitzner discloses a perfumed gel consisting essentially of about 3 to 10 wt % of hydroxypropyl cellulose dissolved in about 90 to 97% of a solution consisting essentially of about 35 to 90% of a linear polyol plasticizer for hydroxypropyl cellulose, 10 to 55% perfume oil and 0 to 10% of a hydroxypropyl cellulose solvent selected from the class consisting of water and 1 to 3 carbon aliphatic alcohols.

Notwithstanding, there remains a continuing need for cost effective, solid non-aqueous gel air odorizer formulations that provide extended, consistent odor control and that offer visual cues regarding the remaining useful life thereof.

The present invention provides a solid non-aqueous gel air odorizer, comprising: 20 to 75 wt % of a poly(propylene oxide); 0.5 to 30 wt % of an ethyl cellulose polymer; 20 to 75 wt % of a $C_{1-5}$ alkyl monoester of a $C_{8-22}$ fatty acid; and 4.5 to 50 wt % of a fragrance; wherein the solid non-aqueous gel air odorizer contains <1.5 wt % water.

The present invention provides a solid non-aqueous gel air odorizer, comprising: 33 to 45 wt % of a poly(propylene oxide); 9 to 11 wt % of an ethyl cellulose polymer; 38 to 50 wt % of isopropyl palmitate; and 8 to 20 wt % of a fragrance; wherein the solid non-aqueous gel air odorizer contains <1.5 wt % water.

BRIEF DESCRIPTION OF THE DRAWING

FIGURE is a graph depicting the weight loss of a solid non-aqueous gel air odorizer over time when exposed to open air at room temperature.

DETAILED DESCRIPTION

We have now found a unique combination of ingredients for a solid non-aqueous gel air odorizer, which combination of ingredients provide consistent delivery of active fragrance, deodorant or insect repellant active over an extended period (at least 30 days; preferably, at least 50 days) and transitions from opaque to clear as the active dissipates.

Unless otherwise indicated, ratios, percentages, parts, and the like are by weight.

As used herein, unless otherwise indicated, the phrase "molecular weight" or Mw refers to the weight average molecular weight as measured in a conventional manner with gel permeation chromatography (GPC) and polyacrylic acid standards. GPC techniques are discussed in detail in Modern Size Exclusion Chromatography, W. W. Yau, J. J. Kirkland, D. D. Bly; Wiley-lnterscience, 1979, and in A Guide to Materials Characterization and Chemical Analysis, J. P. Sibilia; VCH, 1988, p. 81-84. Molecular weights are reported herein in units of Daltons.

The term "polymer" as used herein and in the appended claims refers to a compound prepared by polymerizing monomers, whether of the same or a different type. The generic term "polymer" includes the terms "homopolymer," "copolymer," and "terpolymer."

The term "solid" as used herein and in the appended claims means that the solid non-aqueous gel odorizer will not flow and will substantially retain its shape under moderate stress or pressure (i.e., the force of gravity when placed on a stationary platform) and ambient conditions (i.e., at 1 atm and 25° C.). The degree of rigidity of the solid non-aqueous gel odorizer may range from a dense hardened material (e.g., like concrete) to a resilient flexible material (e.g., like a rubber ball). Preferably, the solid non-aqueous gel odorizer of the present invention will remain solid when exposed to temperatures up to 35° C. (more preferably, 50° C.) with minimal leaching of fragrance.

Preferably, the solid non-aqueous gel air odorizer of the present invention is self-supporting such that the solid non-aqueous gel air odorizer can be used without additional support structure or apparatus.

Preferably, the solid non-aqueous gel air odorizer of the present invention is a solid. More preferably, the solid non-aqueous gel air odorizer of the present invention is a solid and is shape-retaining. Most preferably, the solid non-aqueous gel air odorizer of the present invention is a solid and retains its shape throughout its useful lifetime.

Preferably, the solid non-aqueous gel air odorizer of the present invention is a self-supporting solid that is dry to the touch.

Preferably, the solid non-aqueous gel air odorizer of the present invention, comprises: 20 to 75 wt % (preferably, 20 to 70 wt %; more preferably, 25 to 60 wt %; most preferably, 33 to 45 wt %) of a poly(propylene oxide) (preferably, wherein the poly(propylene oxide) has a weight average molecular weight of 100 to 10,000 (preferably, 200 to 3,000; more preferably, 300 to 1,000; most preferably, 400 to 500)

Daltons); 0.5 to 30 wt % (preferably, 2.5 to 30 wt %; more preferably, 5 to 15 wt %; most preferably, 9 to 11 wt %) of an ethyl cellulose polymer; 20 to 75 wt % (preferably, 20 to 70 wt %; more preferably, 25 to 60 wt %; most preferably, 38 to 50 wt %) of a $C_{1-5}$ alkyl monoester of a $C_{8-22}$ fatty acid (preferably, wherein the $C_{1-5}$ alkyl monoester of the $C_{8-22}$ fatty acid is selected from the group consisting of at least one of isopropyl palmitate, methyl oleate and butyl stearate; more preferably, wherein the $C_{1-5}$ alkyl monoester of a $C_{8-22}$ fatty acid is selected from the group consisting of at least one of isopropyl palmitate and butyl stearate; most preferably, the $C_{1-5}$ alkyl monoester of $C_{8-22}$ fatty acid is isopropyl palmitate); and 4.5 to 50 wt % (preferably, 7.5 to 30 wt %; most preferably, 8 to 20 wt %) of a fragrance; wherein the solid non-aqueous gel air odorizer contains <1.5 wt % water.

Preferably, the poly(propylene oxide) used in the solid non-aqueous gel air odorizer of the present invention has a weight average molecular weight of 100 to 10,000 Daltons. More preferably, the poly(propylene oxide) used in the solid non-aqueous gel air odorizer of the present invention has a weight average molecular weight of 200 to 3,000 Daltons. Still more preferably, the poly(propylene oxide) used in the solid non-aqueous gel air odorizer of the present invention has a weight average molecular weight of 300 to 1,000 Daltons. Most preferably, the poly(propylene oxide) used in the solid non-aqueous gel air odorizer of the present invention has a weight average molecular weight of 400 to 500 Daltons.

Preferably, the solid non-aqueous gel air odorizer of the present invention, comprises 20 to 75 wt % of the poly (propylene oxide), based on weight of the solid non-aqueous gel air odorizer. More preferably, the solid non-aqueous gel air odorizer of the present invention, comprises 20 to 70 wt % of the poly(propylene oxide), based on weight of the solid non-aqueous gel air odorizer. Still more preferably, the solid non-aqueous gel air odorizer of the present invention, comprises 25 to 60 wt % of the poly(propylene oxide), based on weight of the solid non-aqueous gel air odorizer. Most preferably, the solid non-aqueous gel air odorizer of the present invention, comprises 33 to 45 wt % of the poly (propylene oxide), based on weight of the solid non-aqueous gel air odorizer.

Preferably, the solid non-aqueous gel air odorizer of the present invention, comprises 20 to 75 wt % of the poly (propylene oxide), based on weight of the solid non-aqueous gel air odorizer, wherein the poly(propylene oxide) used has a weight average molecular weight of 100 to 10,000 (preferably, 200 to 3,000; more preferably, 300 to 1,000; most preferably, 400 to 500) Daltons. More preferably, the solid non-aqueous gel air odorizer of the present invention, comprises 20 to 70 wt % of the poly(propylene oxide), based on weight of the solid non-aqueous gel air odorizer, wherein the poly(propylene oxide) used has a weight average molecular weight of 100 to 10,000 (preferably, 200 to 3,000; more preferably, 300 to 1,000; most preferably, 400 to 500) Daltons. Still more preferably, the solid non-aqueous gel air odorizer of the present invention, comprises 25 to 60 wt % of the poly(propylene oxide), based on weight of the solid non-aqueous gel air odorizer, wherein the poly(propylene oxide) used has a weight average molecular weight of 100 to 10,000 (preferably, 200 to 3,000; more preferably, 300 to 1,000; most preferably, 400 to 500) Daltons. Most preferably, the solid non-aqueous gel air odorizer of the present invention, comprises 33 to 45 wt % of the poly(propylene oxide), based on weight of the solid non-aqueous gel air odorizer, wherein the poly(propylene oxide) used has a weight average molecular weight of 100 to 10,000 (preferably, 200 to 3,000; more preferably, 300 to 1,000; most preferably, 400 to 500) Daltons.

Preferably, the ethyl cellulose polymer used in the solid non-aqueous gel air odorizer of the present invention has an average ethoxyl content of 45 to 50 wt %. More preferably, the ethyl cellulose polymer used in the solid non-aqueous gel air odorizer of the present invention has an average ethoxyl content of 48 to 50 wt %. Most preferably, the ethyl cellulose polymer used in the solid non-aqueous gel air odorizer of the present invention has an average ethoxyl content of 48 to 49.5 wt %.

Preferably, the ethyl cellulose polymer used in the solid non-aqueous gel air odorizer of the present invention has a viscosity of 90 to 400 cP for a 5 wt % solution (in 80% toluene and 20% ethanol) measured at 25° C. using an Ubbelohde viscometer. More preferably, the ethyl cellulose polymer used in the solid non-aqueous gel air odorizer of the present invention has a viscosity of 180 to 385 cP for a 5 wt % solution (in 80% toluene and 20% ethanol) measured at 25° C. using an Ubbelohde viscometer. Most preferably, the ethyl cellulose polymer used in the solid non-aqueous gel air odorizer of the present invention has a viscosity of 270 to 330 cP for a 5 wt % solution (in 80% toluene and 20% ethanol) measured at 25° C. using an Ubbelohde viscometer.

Preferably, the solid non-aqueous gel air odorizer of the present invention, comprises 0.5 to 30 wt % of the ethyl cellulose polymer, based on weight of the solid non-aqueous gel air odorizer. More preferably, the solid non-aqueous gel air odorizer of the present invention, comprises 2.5 to 30 wt % of the ethyl cellulose polymer, based on weight of the solid non-aqueous gel air odorizer. Still more preferably, the solid non-aqueous gel air odorizer of the present invention, comprises 5 to 15 wt % of the ethyl cellulose polymer, based on weight of the solid non-aqueous gel air odorizer. Most preferably, the solid non-aqueous gel air odorizer of the present invention, comprises 9 to 11 wt % of the ethyl cellulose polymer, based on weight of the solid non-aqueous gel air odorizer.

Preferably, the solid non-aqueous gel air odorizer of the present invention, comprises 0.5 to 30 wt % of the ethyl cellulose polymer, based on weight of the solid non-aqueous gel air odorizer; wherein the ethyl cellulose polymer has a viscosity of 90 to 400 cP (more preferably, 180 to 385 cP; most preferably, 270 to 330 cP) for a 5 wt % solution (in 80% toluene and 20% ethanol) measured at 25° C. using an Ubbelohde viscometer. More preferably, the solid non-aqueous gel air odorizer of the present invention, comprises 2.5 to 30 wt % of the ethyl cellulose polymer, based on weight of the solid non-aqueous gel air odorizer; wherein the ethyl cellulose polymer has a viscosity of 90 to 400 cP (more preferably, 180 to 385 cP; most preferably, 270 to 330 cP) for a 5 wt % solution (in 80% toluene and 20% ethanol) measured at 25° C. using an Ubbelohde viscometer. Still more preferably, the solid non-aqueous gel air odorizer of the present invention, comprises 5 to 15 wt % of the ethyl cellulose polymer, based on weight of the solid non-aqueous gel air odorizer; wherein the ethyl cellulose polymer has a viscosity of 90 to 400 cP (more preferably, 180 to 385 cP; most preferably, 270 to 330 cP) for a 5 wt % solution (in 80% toluene and 20% ethanol) measured at 25° C. using an Ubbelohde viscometer. Most preferably, the solid non-aqueous gel air odorizer of the present invention, comprises 9 to 11 wt % of the ethyl cellulose polymer, based on weight of the solid non-aqueous gel air odorizer; wherein the ethyl cellulose polymer has a viscosity of 90 to 400 cP (more preferably, 180 to 385 cP; most preferably, 270 to 330 cP)

for a 5 wt % solution (in 80% toluene and 20% ethanol) measured at 25° C. using an Ubbelohde viscometer.

Preferably, the $C_{1-5}$ alkyl monoester of a $C_{8-22}$ fatty acid used in the solid non-aqueous gel air odorizer of the present invention is selected to have a Hansen solubility parameter δd (dispersion) of 13.5 to 16; δp (dipolar) of 2 to 8; and δh (hydrogen bonding) of 2 to 8. More preferably, the $C_{1-5}$ alkyl monoester of a $C_{8-22}$ fatty acid used in the solid non-aqueous gel air odorizer of the present invention is selected to have a Hansen solubility parameter δd (dispersion) of 14 to 15; δp (dipolar) of 3 to 5; and δh (hydrogen bonding) of 3 to 5.

Preferably, the $C_{1-5}$ alkyl monoester of a $C_{8-22}$ fatty acid used in the solid non-aqueous gel air odorizer of the present invention is selected from the group consisting of at least one of isopropyl palmitate, methyl oleate and butyl stearate. More preferably, the $C_{1-5}$ alkyl monoester of a $C_{8-22}$ fatty acid used in the solid non-aqueous gel air odorizer of the present invention is selected from the group consisting of at least one of isopropyl palmitate and butyl stearate. Still more preferably, the $C_{1-5}$ alkyl monoester of a $C_{8-22}$ fatty acid used in the solid non-aqueous gel air odorizer of the present invention includes isopropyl palmitate. Most preferably, the $C_{1-5}$ alkyl monoester of a $C_{8-22}$ fatty acid used in the solid non-aqueous gel air odorizer of the present invention is isopropyl palmitate.

Preferably, the solid non-aqueous gel air odorizer of the present invention, comprises 20 to 75 wt % of the $C_{1-5}$ alkyl monoester of a $C_{8-22}$ fatty acid, based on weight of the solid non-aqueous gel air odorizer. More preferably, the solid non-aqueous gel air odorizer of the present invention, comprises 20 to 70 wt % of the $C_{1-5}$ alkyl monoester of a $C_{8-22}$ fatty acid, based on weight of the solid non-aqueous gel air odorizer. Still more preferably, the solid non-aqueous gel air odorizer of the present invention, comprises 25 to 60 wt % of the $C_{1-5}$ alkyl monoester of a $C_{8-22}$ fatty acid, based on weight of the solid non-aqueous gel air odorizer. Most preferably, the solid non-aqueous gel air odorizer of the present invention, comprises 38 to 50 wt % of the $C_{1-5}$ alkyl monoester of a $C_{8-22}$ fatty acid, based on weight of the solid non-aqueous gel air odorizer.

Preferably, the solid non-aqueous gel air odorizer of the present invention, comprises 20 to 75 wt % of the $C_{1-5}$ alkyl monoester of a $C_{8-22}$ fatty acid, based on weight of the solid non-aqueous gel air odorizer; wherein the $C_{1-5}$ alkyl monoester of a $C_{8-22}$ fatty acid is selected from the group consisting of at least one of isopropyl palmitate, methyl oleate and butyl stearate (more preferably, isopropyl palmitate and butyl stearate; most preferably, isopropyl palmitate). More preferably, the solid non-aqueous gel air odorizer of the present invention, comprises 20 to 70 wt % of the $C_{1-5}$ alkyl monoester of a $C_{8-22}$ fatty acid, based on weight of the solid non-aqueous gel air odorizer; wherein the $C_{1-5}$ alkyl monoester of a $C_{8-22}$ fatty acid is selected from the group consisting of at least one of isopropyl palmitate, methyl oleate and butyl stearate (more preferably, isopropyl palmitate and butyl stearate; most preferably, isopropyl palmitate). Still more preferably, the solid non-aqueous gel air odorizer of the present invention, comprises 25 to 60 wt % of the $C_{1-5}$ alkyl monoester of a $C_{8-22}$ fatty acid, based on weight of the solid non-aqueous gel air odorizer; wherein the $C_{1-5}$ alkyl monoester of a $C_{8-22}$ fatty acid is selected from the group consisting of at least one of isopropyl palmitate, methyl oleate and butyl stearate (more preferably, isopropyl palmitate and butyl stearate; most preferably, isopropyl palmitate). Most preferably, the solid non-aqueous gel air odorizer of the present invention, comprises 38 to 50 wt % of the $C_{1-5}$ alkyl monoester of a $C_{8-22}$ fatty acid, based on weight of the solid non-aqueous gel air odorizer; wherein the $C_{1-5}$ alkyl monoester of a $C_{8-22}$ fatty acid is selected from the group consisting of at least one of isopropyl palmitate, butyl stearate and butyl stearate (more preferably, isopropyl palmitate and butyl stearate; most preferably, isopropyl palmitate).

Preferably, the fragrance used in the solid non-aqueous gel air odorizer of the present invention is selected from at least one of a synthetic odorant and a natural odorant.

Preferably, the fragrance used in the solid non-aqueous gel air odorizer of the present invention includes a synthetic odorant. Preferably, the fragrance used in the solid non-aqueous gel air odorizer of the present invention includes a synthetic odorant, wherein the synthetic odorant is selected from the group consisting of at least one of a synthetic product of an ester (e.g., benzyl acetate, phenoxy ethyl isobutyrate, p-tert-butylcyclohexyl acetate, linalyl acetate, dimethyl benzyl carbinyl acetate, phenyl ethyl acetate, linalyl benzoate, benzyl formate, ethyl methyl phenyl glycinate, allyl cyclohexyl propionate, styrallyl propionate, benzyl salicylate, cyclohexyl salicate, floramate, melusate and jasmacyclate); an ether (e.g., benzyl ethyl ether and ambroxan); an aldehyde (e.g., a linear alkanal having 8 to 18 carbon atoms, citral, citronellal, citronellyloxy-acetaldehyde, cyclamen aldehyde, hydroxy citronellal, lilial and bourgeonal); a ketone (e.g., ionone, α-isomethylionone and methyl cedryl ketone); an alcohol (e.g., anethole, citronellol, eugenol, geraniol, linalool, phenylethyl alcohol and terpineol); and a hydrocarbon (e.g., limonene and pinene).

Preferably, the fragrance used in the solid non-aqueous gel air odorizer of the present invention includes a natural odorant. Preferably, the fragrance used in the solid non-aqueous gel air odorizer of the present invention includes a natural odorant, wherein the natural odorant is an extract derived from a plant source (e.g., pine, citrus, jasmine, patchouli, rose, ylang-ylang, clary sage, chamomile, cloves, balm, mint, cinnamon leaf, lime blossom, juniper berry, vetiver, olibanum, galbanum, labdanum, orange blossom, orange peel, sandalwood, lily, lavender, geranium, petitgrain, aniseed, coriander, cumin, nutmeg, bergamot, lemon, maize, angelica, celery, cardamom, costas, iris, calmus, vetiver, guaiac, cedarwood, rosewood, tarragon, lemongrass, thyme, spruce, fir, galbanum, elemi, benzoin, myrrh, olibanum, opoponax, and labdanum) and an animal source (e.g., civet, castoreum).

Preferably, the fragrance used in the solid non-aqueous gel air odorizer of the present invention is selected from the group consisting of at least one of nitriles, sulfides, oximes, acetals, ketals, acids, Schiff bases, heterocyclic nitrogen compounds (e.g., indole, quinoline, pyrazine), amines, amides, organohalogen compounds (e.g., rose acetate), nitrated compounds (e.g., nitromusk), heterocyclic sulfur compounds (e.g., thiazoles) and heterocyclic oxygen compounds.

Preferably, the fragrance used in the solid non-aqueous gel air odorizer of the present invention is selected from the group consisting of orange oil, geraniol, rose oil, lilial, α-hexylcinnamaldehyde, α-amylcinnamaldehyde, propidyl, hexyl salicylate, cedramber, myraldyl acetate, linalool, tetrahydrolinaool, citronellol, Aldehyde C12 lauric, 5-methyl-5-propyl-2-(1-methylbutyl)-1,3-dioxane, diphenyl ether, N-methyl ionone, cyclohexyl salicylate, sandelice and boisambrene forte.

Preferably, the solid non-aqueous gel air odorizer of the present invention, comprises 4.5 to 50 wt % of a fragrance. More preferably, the solid non-aqueous gel air odorizer of the present invention, comprises 7.5 to 30 wt % of a fragrance. Most preferably, the solid non-aqueous gel air odorizer of the present invention, comprises 8 to 20 wt % of a fragrance.

Preferably, the solid non-aqueous gel air odorizer of the present invention, comprises <1.5 wt % water, based on weight of the solid non-aqueous gel air odorizer. More preferably, the solid non-aqueous gel air odorizer of the present invention, comprises <1.0 wt % water, based on weight of the solid non-aqueous gel air odorizer. Still more preferably, the solid non-aqueous gel air odorizer of the present invention, comprises <0.5 wt % water, based on weight of the solid non-aqueous gel air odorizer. Most preferably, the solid non-aqueous gel air odorizer of the present invention, comprises <0.1 wt % water, based on weight of the solid non-aqueous gel air odorizer.

Preferably, the solid non-aqueous gel air odorizer of the present invention, further comprises an optional additive, wherein the optional additive is selected from the group consisting of at least one of a preservative (e.g., Kathon™ preservatives and Neolone® preservatives from The Dow Chemical Company and Lonza, respectively), an antioxidant, a viscosity modifier, a solubility modifier, an antimicrobial agent, a binder, a chelating agent, a fungicide, an aesthetics enhancer and a filler.

Preferably, the solid non-aqueous gel air odorizer of the present invention, further comprises an optional additive, wherein the optional additive includes an aesthetics enhancer selected from the group consisting of at least one of flowers, beads, dyes, pigments (e.g., metallic pigments, thermochromic pigments), photochromic agents, optical brighteners, pearlescent agents, glitters and luminescent agents (e.g., chemiluminescent, bioluminescent).

Potential uses for the solid non-aqueous gel air odorizer of the present invention are broad and varied. The solid non-aqueous gel air odorizer of the present invention can be used as a solid air-freshener with a useful lifetime of >30 days (preferably, >50 days) during which the solid non-aqueous gel air odorizer retains its shape and produce a consistent level of odorization. Given that the solid non-aqueous gel air odorizer of the present invention is self supporting, it does not require costly holders or containers and is amenable to being presented in the form of a shaped object (e.g., in the shape of an animal or flower). The solid non-aqueous gel air odorizer of the present invention is also amenable to being colored. The solid non-aqueous gel air odorizer of the present invention can be provided in a variety of shapes and sizes to facilitate customization for use as air fresheners in HVAC units (e.g., a pellets or flakes of gel incorporated into non-woven filter elements), air fresheners for vehicles (e.g., cars, boats), air fresheners or disinfecting components for use in vacuum cleaners.

Some embodiments of the present invention will now be described in detail in the following Examples.

Comparative Example C1 and Example 1: Solid Non-Aqueous Gel Air Odorizer

Solid non-aqueous gel air odorizer was prepared having the composition set forth in TABLE 1.

TABLE 1

| Material | Concentration in non-aqueous gel air odorizer (wt %) | |
| --- | --- | --- |
| | Comp. Example C1 | Example 1 |
| poly(propylene oxide)[1] | 45 | 40 |
| Isopropyl palmitate[2] | 45 | 40 |
| Ethyl cellulose[3] | 10 | 10 |
| Perfume[4] | 0 | 10 |

[1]Polyglycol P400E polymer available from The Dow Chemical Company
[2]Crodamol ™ IPP isopropyl palmitate available from Croda
[3]Ethocel ™ Std. 300 Industrial grade ethyl cellulose available from The Dow Chemical Company
[4]Exotic Fruits Perfume available from V. Mane et Fils In each of Comparative Example C1 and Example 1, the isopropyl palmitate and the poly(propylene oxide) were combined in a beaker to form a mixture. The ethyl cellulose was then gradually added in powder form to the mixture in the beaker. The beaker contents were then heated at a temperature between 35 and 100° C. with continuous stirring until the ethyl cellulose was completely dissolved. In Example 1, the beaker contents were then allowed to cool to 35° C. and the perfume was added with stirring. In both Comparative Example C1 and Example 1, the beaker contents were then allowed to cool to room temperature and solidify into solid non-aqueous gel air odorizers having the desired shape.

The solid non-aqueous gel air odorizer from each of Comparative Example C1 and Example 1 was then placed in a room and its weight loss over time was then observed and recorded. The results of the observations are depicted in graphical form FIG. 1.

I claim:

1. A solid non-aqueous gel air odorizer, comprising:
   20 to 75 wt %, based on weight of the solid non-aqueous gel air odorizer, of a poly(propylene oxide); wherein the poly(propylene oxide) has a weight average molecular weight of 300 to 1,000 Daltons;
   0.5 to 30 wt %, based on weight of the solid non-aqueous gel air odorizer, of an ethyl cellulose polymer;
   20 to 75 wt %, based on weight of the solid non-aqueous gel air odorizer, of a $C_{1-5}$ alkyl monoester of a $C_{8-22}$ fatty acid; and
   4.5 to 50 wt %, based on weight of the solid non-aqueous gel air odorizer, of a fragrance;
   wherein the solid non-aqueous gel air odorizer contains <1.5 wt %, based on weight of the solid non-aqueous gel air odorizer, water.

2. The solid non-aqueous gel air odorizer of claim 1, further comprising an optional additive, wherein the additive is selected from the group consisting of at least one of a preservative, an antioxidant, a viscosity modifier, a solubility modifier, an antimicrobial agent, a binder, a chelating agent, a fungicide, an aesthetics enhancer and a filler.

3. The solid non-aqueous gel air odorizer of claim 2, wherein the optional additive includes an aesthetics enhancer selected from the group consisting of at least one of flowers, beads, dyes, pigments, photochromic agents, optical brighteners, pearlescent agents, glitters and luminescent agents.

4. The solid non-aqueous gel air odorizer of claim 1, wherein the $C_{1-5}$ alkyl monoester of the $C_{8-22}$ fatty acid is selected from the group consisting of at least one of isopropyl palmitate, methyl oleate and butyl stearate.

5. The solid non-aqueous gel air odorizer of claim 1, wherein the $C_{1-5}$ alkyl monoester of the $C_{8-22}$ fatty acid is isopropyl palmitate.

6. The solid non-aqueous gel air odorizer of claim 5, wherein the poly(propylene oxide) has a weight average molecular weight of 400 to 500 Daltons.

7. The solid non-aqueous gel air odorizer of claim 6, further comprising an optional additive, wherein the optional additive is selected from the group consisting of at least one of a preservative, an antioxidant, a viscosity modifier, a solubility modifier, an antimicrobial agent, a binder, a chelating agent, a fungicide, an aesthetics enhancer and a filler.

8. The solid non-aqueous gel air odorizer of claim 6, wherein the solid non-aqueous gel air odorizer includes:
   33 to 45 wt % of the poly(propylene oxide);
   9 to 11 wt % of the ethyl cellulose polymer;
   38 to 50 wt % of the isopropyl palmitate;
   8 to 20 wt % of the fragrance.

* * * * *